United States Patent [19]

Moore et al.

[11] Patent Number: 5,411,743
[45] Date of Patent: May 2, 1995

[54] PREVENTION OF SYNOVIAL ADHESIONS

[75] Inventors: Larry J. Moore; Jill Adler-Moore, both of Altadena, Calif.

[73] Assignee: Vestar, Inc., San Dimas, Calif.

[21] Appl. No.: 157,841

[22] Filed: Nov. 23, 1993

Related U.S. Application Data

[63] Continuation of Ser. No. 621,625, Dec. 3, 1990, abandoned.

[51] Int. Cl.⁶ .............................................. A61K 9/127
[52] U.S. Cl. .................................. 424/450; 514/825
[58] Field of Search ............... 424/450; 260/403; 428/402.2; 264/4.1, 4.3, 4.4; 436/9; 514/825

[56] References Cited

U.S. PATENT DOCUMENTS

| | | | |
|---|---|---|---|
| 4,346,108 | 8/1982 | Singer | 424/317 |
| 4,427,649 | 1/1984 | Dingle et al. | 424/38 |
| 4,482,554 | 11/1984 | Gebhardt et al. | 424/246 |
| 4,877,619 | 10/1989 | Richer | 424/450 |
| 4,937,254 | 6/1990 | Sheffield et al. | 514/420 |
| 4,971,802 | 11/1990 | Tarcsay et al. | |

FOREIGN PATENT DOCUMENTS

| | | |
|---|---|---|
| 1246446 | 12/1988 | Canada . |
| 0225162 | 6/1987 | European Pat. Off. . |
| 0249561 | 12/1987 | European Pat. Off. . |
| 2712031 | 9/1977 | Germany . |
| 2217596 | 11/1989 | United Kingdom . |
| WO8901777 | 3/1989 | WIPO . |

OTHER PUBLICATIONS

Holmlund et al., Arthroscopy of the rabbit temporomandibula joint, (1986) Int. J. Oral Maxillofac. Surg. 15, 170–175.

Wheater et al., Functional Histology, 2nd Edition (1987) Churchill Livingstone, Edinburgh, pp. 64, 65, 158, 204, 297.

Physicians' Desk Reference, 43rd Edition (1989) pp. 1242–1243.

Webster's dictionary, p. 1151, 1984.

International Search Report of PCT/US91/09017 mailed Apr. 16, 1992.

"Intra-articular Liposomal Therapy", Thomas and Phillips, Chapter 21, 1979.

"Use of Hyaluronic Acid Ester Microspheres in the Treatment of Rheumatoid Arthritis" Hume et al., Proceed.Intern.Symp.Control.Rel.Bioact.Mater. 17(1990).

*Primary Examiner*—Gollamudi S. Kishore
*Attorney, Agent, or Firm*—Adam Cochran; George A. Gilbert

[57] ABSTRACT

Adhesions in synovial capsules are prevented through the administration of liposome intercalated nonsteroidal anti-inflammatory agents.

3 Claims, No Drawings

PREVENTION OF SYNOVIAL ADHESIONS

This a continuation of application Ser. No. 7/621,625 filed on 03 Dec. 1990, now abandoned.

FIELD OF THE INVENTION

This invention relates to the field of biochemistry and medicine, and more particularly to methods for the prevention of adhesions in traumatized synovial tissue.

BACKGROUND AND SUMMARY OF THE INVENTION

The mammalian body is replete with joint spaces, that is, areas which comprise an articulating mechanism for the movement of limbs and other members. These joint spaces are also known as synovial capsules. Joint spaces include synovial tissue, which supplies a lubricating synovia (fluid) for the articulating members.

Trauma to the joint space, whether as a result of injury or surgery, often produces adhesions within the joint space which is accompanied by further destruction of the synovial tissue (disk perforation and other secondary trauma) which interferes with healing and proper functioning of the joint.

While work has been performed in an attempt to limit the formation of adhesions in unrelated parts of the mammalian body (e.g., the formation of adhesions in peritoneal surgery) the joint space differs significantly from other areas of the body and efforts to prevent adhesions within the joint spaces, particularly following arthroscopic surgery, have been unsuccessful. Thus, it has been a desideratum to provide a method to prevent adhesions in the synovial capsule.

According to the invention, a method is provided for the prevention of adhesion formation in a synovial joint space, which comprises the administration of a lipid particle intercalated nonsteroidal anti-inflammatory agent to the synovial joint space in an amount which is effective for the treatment.

DETAILED DESCRIPTION OF THE INVENTION

A wide variety of lipid particles may include a nonsteroidal antiinflammatory agent to form the vesicles of the invention, which are capable of preventing the formation of adhesions in a synovial capsule. For example, the delivery vehicles disclosed in the Vestar, Inc. patent publication EP0272091 (the counterpart of U.S. Ser. No. 942,093 filed 15 Dec. 1986), may be employed. These vehicles are composed of a single encapsulating phospholipid membrane associated with an amphiphile-associated substrate. However, the lipid particles are preferably comprised of phospholipids and most preferably are liposomes.

Phospholipids are amphipathic molecules which are the primary constituents of cell membranes. Typical phospholipid hydrophilic groups include phosphatidylcholine and phosphatidylethanolamine moieties, while typical hydrophobic groups include a variety of saturated and unsaturated fatty acid moieties. Mixture of a phospholipid in water causes spontaneous organization of the phospholipid molecules into a variety of characteristic phases depending on the conditions used. These include bilayer structures in which the hydrophilic groups of the phospholipids interact at the exterior of the bilayer with water, while the hydrophobic groups interact with similar groups on adjacent molecules in the interior of the bilayer. Such bilayer structures can be quite stable and form the principal basis for cell membranes.

Phospholipid bilayer structures can also be formed into closed spherical shell-like structures which are called phospholipid vesicles or liposomes. The membrane bilayers in these structures typically encapsulate an aqueous volume, and form a permeability barrier between the encapsulated volume and the exterior solution. Phospholipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1–10 $\mu$m (1000–10,000 nm). Sonication of these structures, or other methods known in the art, leads to formation of unilamellar vesicles (UVs) having an average diameter of about 30–300 nm. However, the range of 50 to 100 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. No. 4,753,788 to Ronald C. Gamble and U.S. Pat. No. 4,935,171 to Kevin R. Bracken.

Either as MLVs or UVs, liposomes have proven valuable as vehicles for drug delivery in animals and in humans. Active drugs, including small hydrophilic molecules and polypeptides, can be trapped in the aqueous core of the liposome, while hydrophobic substances can be dissolved in the liposome membrane. The liposome structure can be readily injected and form the basis for both sustained release and drug delivery to specific cell types, or parts of the body. MLVs, primarily because they are relatively large, are usually rapidly taken up by the reticuloendothelial system (the liver and spleen). The invention typically utilizes vesicles which remain in the circulatory system for hours and break down after internalization by the target cell. For these requirements the formulations preferably utilize UVs having a diameter of less than 200 nm, preferably less than 100 nm. Preferred liposome compositions include various mole ratios of distearoylphosphatidylcholine (DSPC) and dipalmitoylphosphatidylcholine (DPPC) and cholesterol. The preferred liposomes consist of a 2:1 mole ratio of DSPC and cholesterol.

Nonsteroidal anti-inflammatory drugs and prodrugs include azapropazone, carprofen, diclofenac sodium, fenamic acids, fenbufen, fenclofenac, flurbiprofen, ibuprofen, ketoprofen, naproxen, oxaprozin, tolmetin sodium, piroxicam and related oxicams.

The lipid particle/nonsteroidal anti-inflammatory composition of the invention is preferably administered to the joint space by injection (or as part of the arthroscopic irrigation fluid) after trauma or surgery, so that a bolus of the agent remains in the synovial capsule following the trauma. From the example which follows, one of ordinary skill can easily determine the dose which is effective. Generally, the solution which comprises the composition should be isotonic.

Temporomandibular joint (TMJ) disorder is a common problem affecting young to middle aged adults, resulting in pain, suffering, and loss of productivity.

TMJ disorder may be divided into two distinct entities, myofascial pain dysfunction syndrome, and internal derangement. Internal derangement is a surgical disease requiring arthroscopic surgery or open arthroplasty for relief of pain and improved function.

Arthroscopic surgery of the human TMJ has revealed a high frequency of intraarticular adhesions in patients with internal derangements. These adhesions arise from traumatic or iatrogenic injuries to the soft tissues of the joint. Postsurgical adhesions play an important role in those surgeries which fail to restore normal range of motion and function.

Various modalities are currently used to reduce inflammation and prevent the formation of new adhesions following arthroscopic or open TMJ surgery. Corticosteroid suspensions, injected into the joint at surgery, are widely employed to minimize postsurgical inflammation. However, serious side effects have long been associated with intraarticular steroid use, including destructive arthropathy. Other agents have been used, including hyaluronic acid salts and hyaluronidase. Hyaluronate is used as a lubricant, while hyaluronidase is supposed to inhibit adhesion of exposed ground substance in injured tissues. No published studies support the efficacy of either agent in preventing postoperative adhesions in the TMJ.

In spite of successful surgical mobilization, intraarticular corticosteroids, and appropriate physical therapy, failure rates following TMJ surgery are approximately 15 to 27%. The formation of new adhesions after surgery is believed to be a principal factor in failure of surgical therapy.

A model exists, as described in the examples below, in which adhesions which result from arthroscopic surgery such as TMJ adhesions can be reliably induced in the rabbit. The rabbit has been used frequently as a model for human TMJ surgery due to similarities in form and function, and adequate size and accessibility.

EXAMPLES 1

Preparation of the Composition

L-alpha-distearoyl phosphatidylcholine ("DSPC"), 1.21 g, and 0.29 g cholesterol (molar ratio of DSPC to cholesterol is 2:1) and 4.3 mole % alpha-tocopherol were dissolved in a suitable solvent (chloroform), with heat and agitation to a minimum concentration of approximately 30% (w/v). The lipid was then spray dried to a fine powder in a spray drying apparatus using an air-nitrogen mixture. Example operating conditions include an air temperature of 71° C., air input of 3.5–4.5 $m^3$/min, a nozzle setting of 1.5–2.0 kg/$cm^2$ and a feed rate of 5–8 ml/min. Na-tolmetin in sterile, pyrogen-free phosphate buffered saline was added to the spray dried lipid components to effect a final concentration of 30 mg/ml of drug and 120 mg/ml of lipid. The materials were vortex-stirred for 40 to 60 minutes in a 65° C. water bath under nitrogen to form MLVs and then autoclaved. Prior to use, the MLVs were diluted 1:3 with phosphate-buffered saline.

Prevention of Adhesions in TMJ Arthroscopy

Twenty-one female New Zealand White rabbits weighing 2.73 to 3.75 kg received autogenous dermal grafts to the temporomandibular joints (TMJs) bilaterally for reconstruction of surgically created defects of the disk. This procedure is known to produce intraarticular adhesions. Three joints were unoperated to serve as normal controls. General anesthesia was induced with Ketamine 50 mg/kg IM, and maintained by inhalation of Forane and $N_2O/O_2$. 300,000 units of procaine penicillin was injected intramuscularly prior to surgery. Surgical defects were created with a scalpel at the junction of the disk and posterior attachment tissues. The 2 by 3 mm defect was then repaired with autogenous dermis harvested from the lateral thigh. The grafts were secured with four sutures of 6–0 mersiline. The TMJ capsules were closed with 5–0 Vicryl sutures, and the superior joint spaces injected with 0.5 ml of one of the following: Lactated Ringer's solution (operated control)-10 joints, Tolmetin liposomes 10 mg/ml-9 joints, sodium hyaluronate 10 mg/ml-10 joints, dexamethasone acetate 8 mg/ml-10 joints. The control or experimental substances were supplied to the surgeon in covered syringes in a randomized double blind fashion. The skin incisions were closed with 3- 0 chromic gut sutures and dressed with triple antibiotic ointment. All the rabbits survived surgery and gained weight in the postoperative period. Half the animals were sacrificed at 4 weeks postoperative, and the remaining animals were sacrificed at 8 weeks postoperative.

Gross dissection of the operated TMJs revealed severe adhesions in 10/10 joints treated with lactated Ringer's solution, moderate to severe adhesions in 10/10 joints treated with hyaluronate, mild, moderate or severe adhesions in 10/10 joints treated with dexamethasone, and mild adhesions in 2/9 joints treated with Tolmetin liposomes (7 of 9 joints were adhesion-free).

Based on nonparametric statistical analysis of the results of gross dissections, tolmetin liposomes show significant reduction in formation of experimentally induced adhesions in the rabbit TMJ. Hyaluronate and dexamethasone showed no significant reduction in adhesions over lactated Ringer's controls.

We claim:

1. A method for the prevention of adhesion formation in a synovial tissue, produced by trauma or surgery, comprising the administration of liposomal intercalated tolmetin to the synovial tissue in an amount which is effective for such prevention.

2. The method of claim 1 in which said liposomes are multilamellar vesicles.

3. The method of claim 1 in which said liposomes are unilamellar vesicles.

* * * * *